(12) United States Patent
Nakai (10) Patent No.: US 9,645,086 B2
(45) Date of Patent: May 9, 2017

(54) COMPONENTIAL ANALYSIS METHOD, COMPONENTIAL ANALYSIS APPARATUS AND NON-TRANSITORY COMPUTER-READABLE RECORDING MEDIUM

(71) Applicant: KABUSHIKI KAISHA TOSHIBA, Minato-Ku, Tokyo (JP)

(72) Inventor: Takehiro Nakai, Yokkaichi (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 353 days.

(21) Appl. No.: 14/199,732

(22) Filed: Mar. 6, 2014

(65) Prior Publication Data

US 2015/0062574 A1 Mar. 5, 2015

Related U.S. Application Data

(60) Provisional application No. 61/872,324, filed on Aug. 30, 2013.

(51) Int. Cl.
*G01J 3/44* (2006.01)
*G01N 21/65* (2006.01)

(52) U.S. Cl.
CPC .................. *G01N 21/65* (2013.01)

(58) Field of Classification Search
CPC ...................................................... G01N 21/65
USPC ....................................................... 356/301
See application file for complete search history.

(56) References Cited

U.S. PATENT DOCUMENTS

| | | | |
|---|---|---|---|
| 6,379,920 B1 * | 4/2002 | El-Sayed | C12Q 1/02 435/29 |
| 7,295,307 B2 | 11/2007 | Naka et al. | |
| 7,327,444 B2 | 2/2008 | Naka et al. | |
| 8,570,507 B1 * | 10/2013 | Cooper | G01J 3/44 356/301 |
| 2003/0008401 A1 * | 1/2003 | Berndt | G01N 15/1012 436/8 |
| 2006/0038980 A1 * | 2/2006 | Naka | G01N 21/65 356/73 |
| 2009/0287374 A1 * | 11/2009 | Kuramori | B60W 40/08 701/41 |

(Continued)

FOREIGN PATENT DOCUMENTS

JP 10-335263 A 12/1998
JP 2005-201756 A 7/2005

(Continued)

*Primary Examiner* — Hina F Ayub
(74) *Attorney, Agent, or Firm* — Holtz, Holtz & Volek PC (57) ABSTRACT

In accordance with an embodiment, a componential analysis method includes dividing a sample structure into at least a first layer to be analyzed and a second layer located closer to a surface layer of the sample than the first layer, applying, to the sample, laser lights of first and second wavelengths respectively corresponding to the depths of the first and second layers, detecting Raman scattered lights respectively obtained from the sample by the application of the laser lights and then outputting first and second Raman signals, spectrally processing the first and second Raman signals to acquire first and second Raman spectrums, acquiring a differential spectrum by subtracting the second Raman spectrum from the first Raman spectrum, and analyzing the differential spectrum.

6 Claims, 11 Drawing Sheets

(56) References Cited

U.S. PATENT DOCUMENTS

| | | | |
|---|---|---|---|
| 2010/0014078 A1* | 1/2010 | Dholakia | G01J 3/28 356/301 |
| 2011/0178379 A1* | 7/2011 | Dudhia | A61B 5/0075 600/310 |
| 2011/0208063 A1* | 8/2011 | Papazoglou | A61B 5/0059 600/473 |
| 2012/0241846 A1 | 9/2012 | Kawasaki et al. | |
| 2013/0094273 A1* | 4/2013 | Chien | G11C 5/06 365/63 |
| 2014/0295213 A1* | 10/2014 | Jalaguier | B05D 3/14 428/704 |

FOREIGN PATENT DOCUMENTS

| | | |
|---|---|---|
| JP | 2009-032855 A | 2/2009 |
| JP | 2009-168562 A | 7/2009 |

\* cited by examiner

COMPONENTIAL ANALYSIS METHOD, COMPONENTIAL ANALYSIS APPARATUS AND NON-TRANSITORY COMPUTER-READABLE RECORDING MEDIUM

CROSS-REFERENCE TO RELATED APPLICATIONS

This application is based upon and claims the benefit of U.S. provisional Application No. 61/872,324, filed on Aug. 30, 2013, the entire contents of which are incorporated herein by reference.

FIELD

Embodiments described herein relate generally to a componential analysis method, a componential analysis apparatus, and a non-transitory computer-readable recording medium.

BACKGROUND

In order to improve the yield of semiconductor products, it is important for process improvements to detect a defect in a manufacturing process at an early stage in an analysis to evaluate how the process has been completed.

TEM electron beam diffraction, EELS, and EDX analysis have heretofore been used to analyze the crystallinity and composition of a given layer in a sample. However, these analysis methods are destructive analyses that require the sample to be processed into flakes, and are therefore unsuitable for line monitoring. Raman spectroscopy is an evaluation method that does not necessarily require the sample processing, and can obtain a Raman peak corresponding to the crystal structure of an analysis target layer. Therefore, the Raman spectroscopy is a technique that is effective in the nondestructive line monitoring.

The Raman spectroscopy requires a laser light source which excites molecular vibration. Since the penetration depth into a sample to be measured is determined depending on the wavelength of a laser light, it is necessary to select a wavelength in accordance with the depth of a target layer when a structure is evaluated. When a sample is a semiconductor device having a stack structure and is evaluated in the direction perpendicular to its upper surface, information that can be obtained in the depth direction varies by a laser wavelength to be selected.

The above-mentioned conventional evaluation method is effective when the number of stacked layers in the structure is small. However, for example, as in a three-dimensionally stacked semiconductor storage device, the number of stacked layers in a structure has been increasing in recent years. Even a single layer may be increasing in thickness. It has been increasingly difficult to extract information at a desired layer in the multilayer structure and information at a position of an arbitrary depth in thick layers.

DETAILED DESCRIPTION

In accordance with an embodiment, a componential analysis method includes dividing a sample structure into at least a first layer to be analyzed and a second layer located closer to a surface layer of the sample than the first layer, applying, to the sample, laser lights of first and second wavelengths respectively corresponding to the depths of the first and second layers, detecting Raman scattered lights respectively obtained from the sample by the application of the laser lights and then outputting first and second Raman signals, spectrally processing the first and second Raman signals to acquire first and second Raman spectrums, acquiring a differential spectrum by subtracting the second Raman spectrum from the first Raman spectrum, and analyzing the differential spectrum.

Embodiments will now be explained with reference to the accompanying drawings. Like components are provided with like reference signs throughout the drawings and repeated descriptions thereof are appropriately omitted. It is to be noted that the term "approximately" is used to include measurement errors in the present application.

(A) Componential Analysis Apparatus (1) Apparatus Configuration

Figure 1:
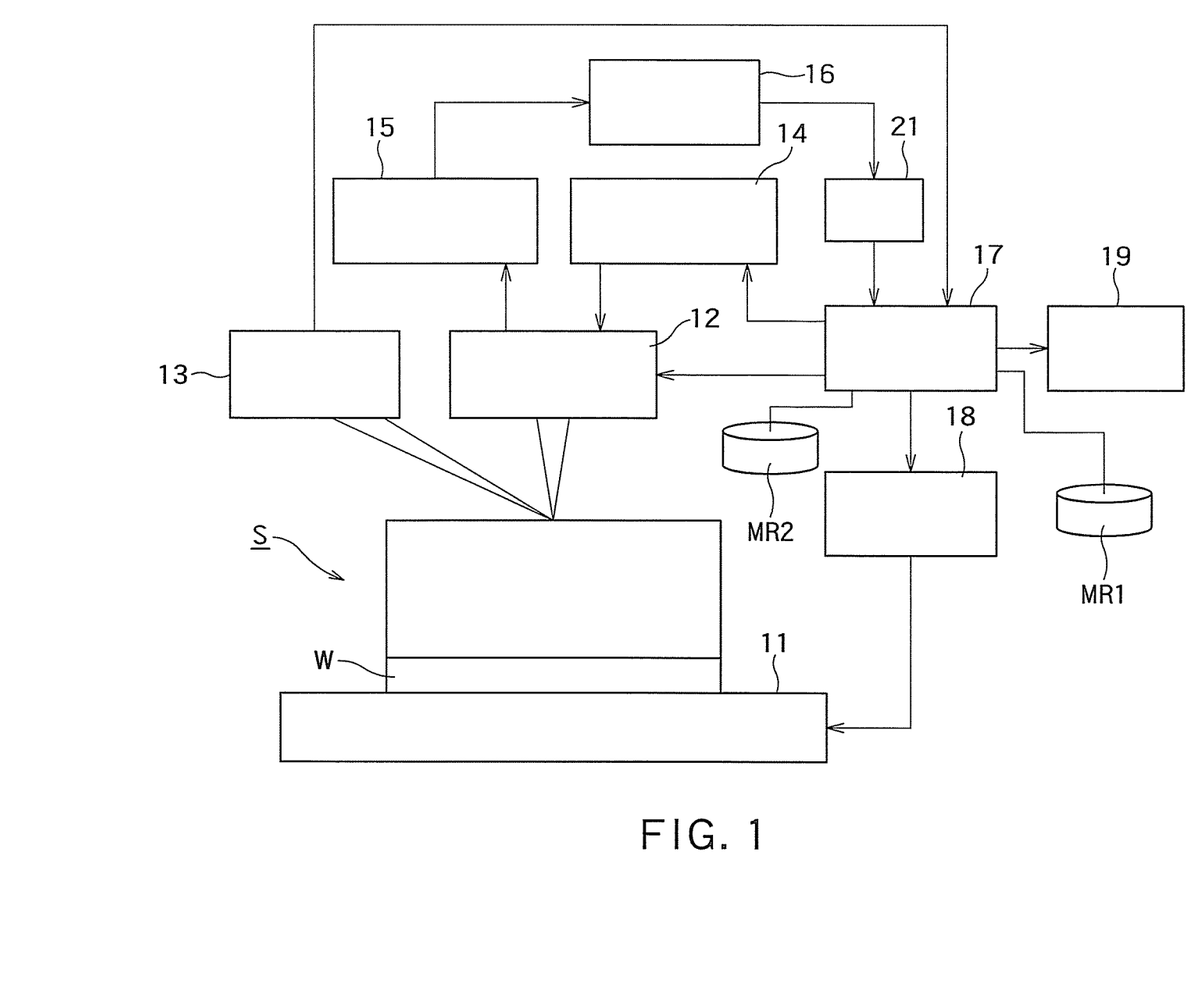
FIG. 1 is a block diagram showing the general configuration of a componential analysis apparatus according to one embodiment.

FIG. 1 is a block diagram showing the general configuration of a componential analysis apparatus according to one embodiment. The componential analysis apparatus shown in FIG. 1 includes a control computer 17, a stage controller 18, a stage 11, a laser optical system 12, an analysis position depth measurement unit 13, a laser scanning control unit 14, a detection unit 15, a spectral processing unit 16, an analysis unit 21, and a display unit 19.

The stage 11 holds a sample S. In accordance with a control signal sent from the stage controller 18, the stage 11 moves the sample S in a horizontal direction (X-Y direction)

via an unshown actuator so that laser light enters a target position on the sample S. The stage controller 18 generates the control signal to move the stage 11 in accordance with a signal from the control computer 17. The analysis position depth measurement unit 13 uses, for example, a spectroscopic ellipsometer to measure the depth of an analysis target position in the sample S, and sends the measurement result to the control computer 17.

In accordance with the measurement result from the analysis position depth measurement unit 13, the control computer 17 calculates a wavelength for the laser light to penetrate into the analysis target position, and supplies the calculation result to the laser scanning control unit 14. The laser scanning control unit 14 generates a control signal in accordance with the wavelength information supplied from the control computer 17, and sends the control signal to the laser optical system 12. The laser optical system 12 is provided with a plurality of laser light sources which generate laser lights different in wavelength. In accordance with the control signal sent from the laser scanning control unit 14, the laser optical system 12 selects a laser light source to apply the laser light to the sample S. In the present embodiment, the laser optical system 12 corresponds to, for example, an application unit.

The detection unit 15 detects a Raman scattered light obtained from the sample S by the application of the laser light and then outputs a Raman signal, and sends the Raman signal to the spectral processing unit 16. The spectral processing unit 16 spectrally processes the Raman signal sent from the detection unit 15, and calculates a differential spectrum and sends the differential spectrum to the analysis unit 21. The differential spectrum will be described later in detail.

The analysis unit 21 analyzes the differential spectrum sent from the spectral processing unit 16 to analyze the components of a material at the analysis target position. The analytic result is displayed by the display unit 19, and stored in a memory MR2.

The control computer 17 is connected to the laser scanning control unit 14, the laser optical system 12, and the stage controller 18, and generates various control signals and then sends the control signals to these units. The control computer 17 is also connected to the memory MR1. A recipe file in which specific procedures of a componential analysis described later are written is stored in the memory MR1. The control computer 17 reads the recipe file from the memory MR1, and then executes a series of componential analyses.

(2) Operation

The operation of the componential analysis apparatus shown in FIG. 1 is described with reference to FIG. 2 to FIG. 11. A structure including a three-dimensionally stacked semiconductor memory provided on a semiconductor substrate W is shown as an example of the sample S.

Figure 2:
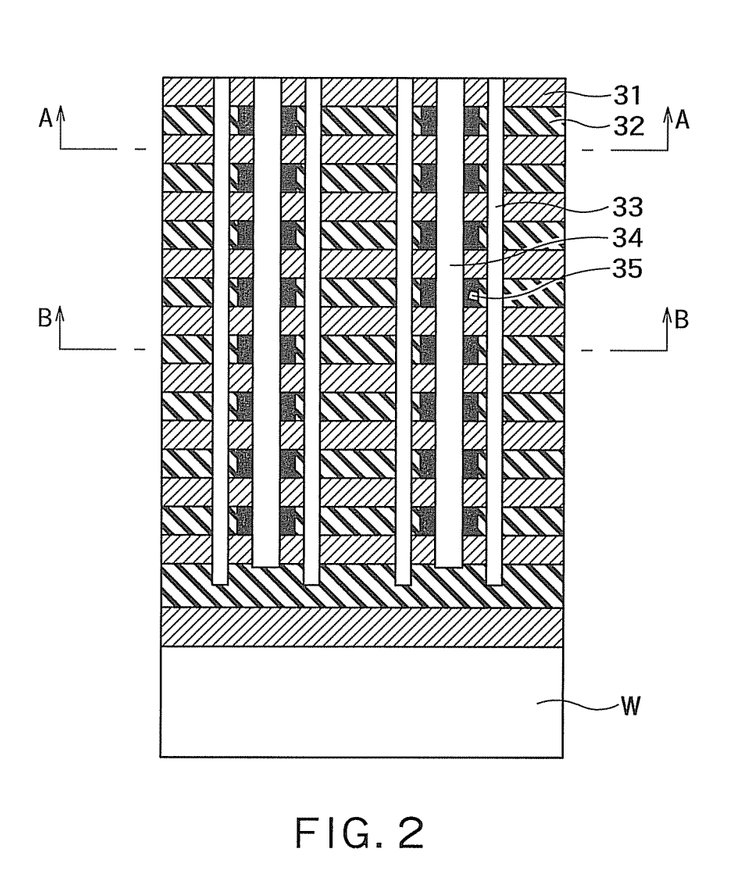
FIG. 2 is a schematic sectional view showing an example of a sample.
Figure 3:
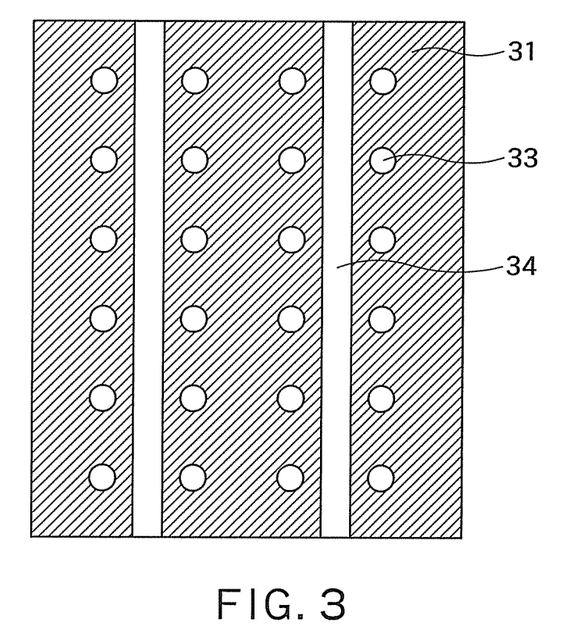
FIG. 3 is a partial top view taken along the line A-A in FIG. 2.
Figure 4:
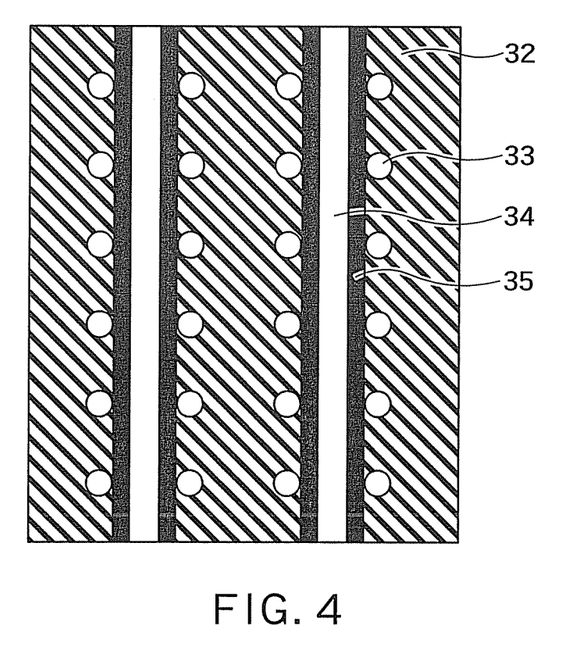
FIG. 4 is a partial top view taken along the line B-B in FIG. 2.

FIG. 2 is a schematic sectional view showing the structure in the three-dimensionally stacked semiconductor memory. FIG. 3 is a top view taken along the line A-A in FIG. 2. FIG. 4 is a top view taken along the line B-B in FIG. 2. In the structure shown in FIG. 2 to FIG. 4, multi-layered insulating films 31 and multi-layered electrically conductive films 32 are alternately stacked. In this stack, contact holes 33, and slits 34 for element separation and isolation are provided. The electrically conductive films 32 are made of, for example, polycrystalline silicon. The insulating films 31 are made of, for example, silicon oxide films or silicon nitride films. A metal silicide is formed on the sides of the electrically conductive films 32 that face the slits 34. In the present embodiment, the metal silicide is nickel silicide 35. The nickel silicide 35 may be formed after the formation of the slits 34, or the slits 34 may be formed after the formation of the nickel silicide 35. The metal silicide is not at all limited to the nickel silicide. For example, other metal silicides such as titanium silicide and cobalt silicide can be analysis targets if these metal silicides allow a Raman signal derived from a silicide crystal structure to be obtained.

The structure shown in FIG. 2 to FIG. 4 is in the process of manufacture, and the structures of elements and wiring lines to be formed in the subsequent processes are not shown. The contact holes 33 are regularly arranged with an equal pitch in FIG. 2 to FIG. 4, but may be irregularly arranged. The slits 34 are refilled in the subsequent process.

Figure 5:
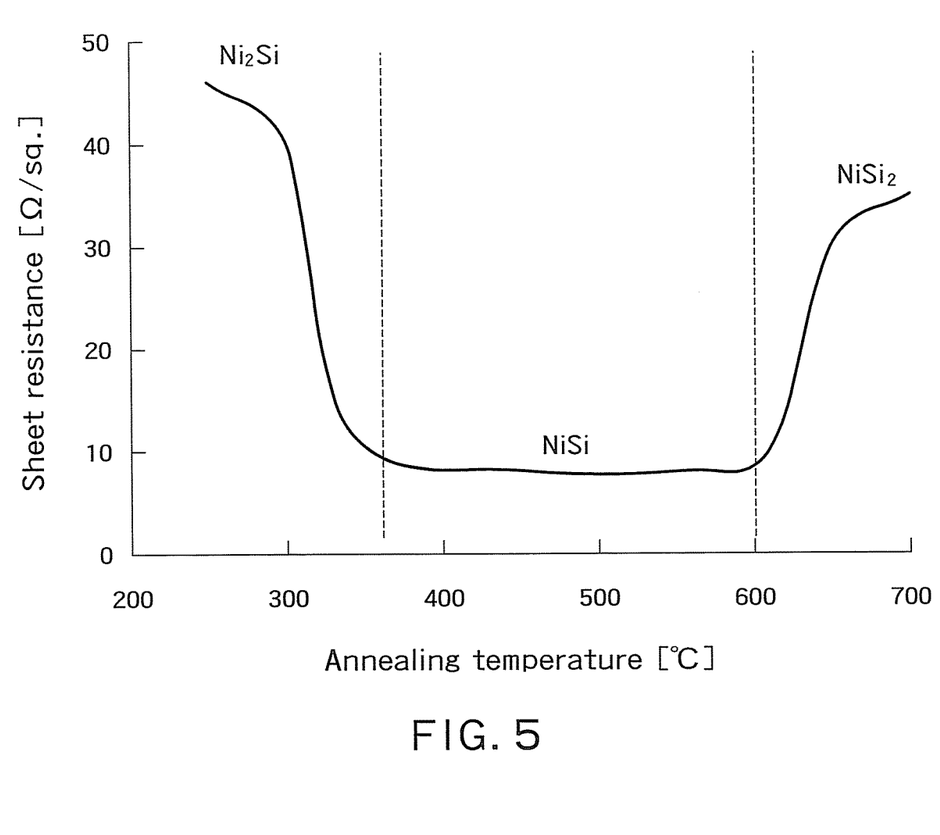
FIG. 5 is a graph illustrating a silicidation reaction of nickel silicide.

Now, the crystal structure of the nickel silicide 35 and the Raman signal corresponding to the thermal treatment dependence of sheet resistance and each crystal structure are described with reference to FIG. 5 and FIG. 6. In a silicidation reaction of the nickel silicide 35, the crystal structure changes in such a manner as $Ni_2Si \rightarrow NiSi \rightarrow NiSi_2$ because of a high-temperature thermal treatment (annealing), as shown in a graph of FIG. 5. The sheet resistance also changes with this change of the crystal structure. In general, NiSi having a low resistance value will be a target structure in a semiconductor process.

Figure 6:
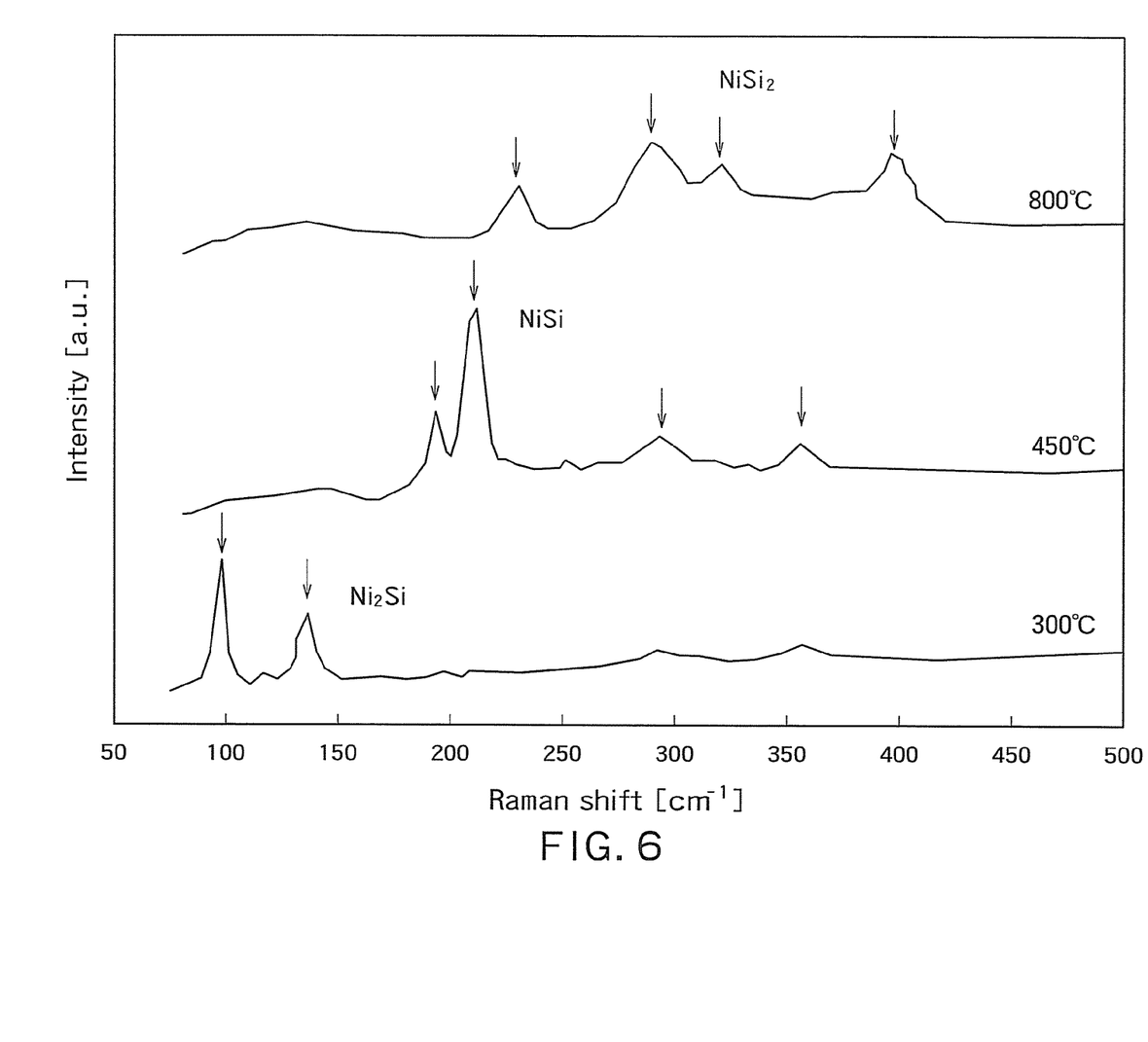
FIG. 6 is a graph showing an observation example of Raman signals obtained regarding nickel silicide.

FIG. 6 is a graph showing an example of a Raman profile which has been measured from nickel silicide formed on a blanket wafer. In the measurement example shown in FIG. 6, peaks of $Ni_2Si$ appear from 90 to 150 $cm^{-1}$ at 300° C., peaks of NiSi appear from 180 to 370 $cm^{-1}$ at 450° C., and peaks of $NiSi_2$ appear from 230 to 400 $cm^{-1}$ at 800° C. Therefore, changes in the crystal structure of the metal silicide can be monitored by the evaluation of these peak intensities. In the present embodiment, the Raman profile shown in FIG. 6 corresponds to, for example, a reference spectrum.

As described above, when a semiconductor device having a stack structure is evaluated in the direction perpendicular to its upper surface, information that can be obtained varies in the depth direction by a laser wavelength to be selected. By way of example, the penetration depth of laser into silicon crystal is 10 nm in the case of a light having a wavelength of 364 nm, 980 nm in the case of a light having a wavelength of 488 nm, or 3920 nm in the case of a light having a wavelength of 647 nm. According to Raman spectroscopy with back-scattering geometry, about half the above depth is the penetration depth at which the Raman signal can be obtained.

Figure 7:
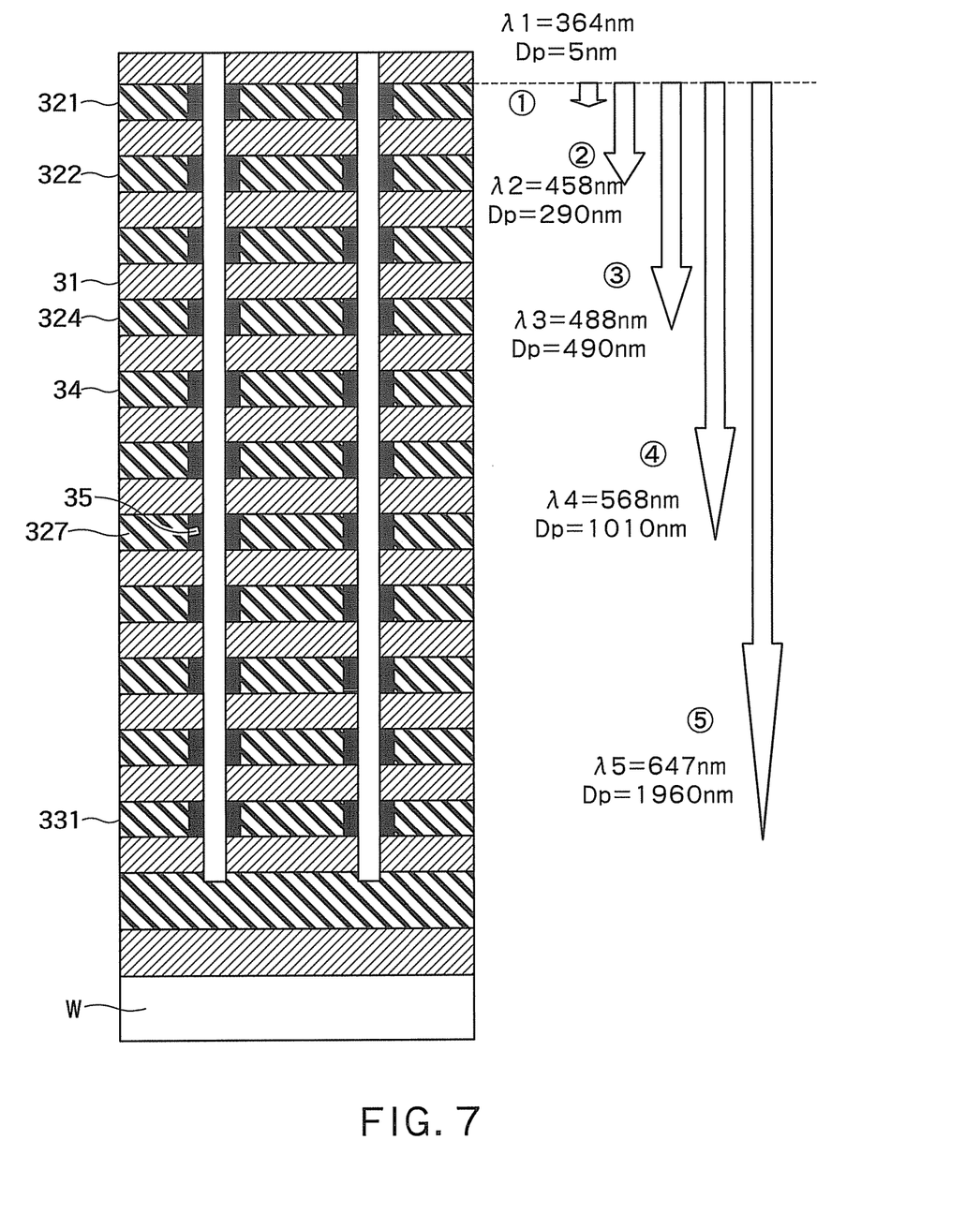
FIG. 7 is a diagram showing a sectional view of an example of a three-dimensionally stacked semiconductor memory during a process, together with the penetration depths of laser lights at which the Raman signals are obtained.

FIG. 7 is a diagram showing a sectional view shown in FIG. 2 together with the penetration depths of laser lights at which the Raman signals are obtained. Each memory cell in the structure shown in FIG. 2 has a height of approximately 2 μm. The inspection target is not at all limited to the above thickness, and the components of a substance having a thickness ranging from several nm to several hundred nm can be analyzed.

Arrows shown on the right side of the three-dimensional stack in FIG. 7 represent penetration depths at which the Raman signals are obtained when excitation lasers having several kinds of wavelengths are used. The penetration depth is a calculated value at half the silicon penetration depth. Since the outermost insulating film of the three-dimensional stack transmits light, the light is not attenuated here, and it is assumed that the attenuation of the light starts in the first electrically conductive film.

First, an unshown conveyer is used to mount the sample S onto the stage 11 and the sample S is held by the stage 11. Also using an unshown alignment mechanism, the stage controller 18 then horizontally aligns the sample S in accordance with the control signal from the control computer 17.

The analysis position depth measurement unit 13 then measures the height of the componential analysis target position, that is, the penetration depth of the laser light by an absorption coefficient calculation based on, for example, the spectroscopic ellipsometer, and sends the measurement result to the control computer 17. According to the present embodiment, as shown in FIG. 7, the three-dimensional stack is divided into five layers, and the values of central depths Dp=5 nm, 290 nm, 490 nm, 1010 nm, and 1960 nm of the lowermost electrically conductive layers in the respective divisions are acquired. When the penetration depth of the laser light can be previously found from, for example, design information, numerical values may be input to the control computer 17 via an unshown input unit without sequential use of the analysis position depth measurement unit 13.

In accordance with the measurement result or input value from the analysis position depth measurement unit 13, the control computer 17 then calculates a wavelength for the laser light to penetrate into the analysis target position. According to the present embodiment, as shown in FIG. 7, wavelengths $\lambda 1$=364 nm, $\lambda 2$=458 nm, $\lambda 3$=488 nm, $\lambda 4$=568 nm, and $\lambda 5$=647 nm are calculated for depths Dp=5 nm, 290 nm, 490 nm, 1010 nm, and 1960 nm, respectively. The control computer 17 supplies these calculation results to the laser scanning control unit 14. The laser scanning control unit 14 generates a control signal in accordance with the supplied wavelength information, and sends the control signal to the laser optical system 12. In accordance with the control signal from the laser scanning control unit 14, the laser optical system 12 applies the above-mentioned laser light of each wavelength to the sample S.

A Raman scattered light is generated from the sample S in response to the application of the laser light of each wavelength. For example, the detection unit 15 detects the Raman scattered lights respectively generated from an electrically conductive layer (first conductive layer from the outermost layer) 321, an electrically conductive layer (second conductive layer from the outermost layer) 322, an electrically conductive layer (fourth conductive layer from the outermost layer) 324, an electrically conductive layer (seventh conductive layer from the outermost layer) 327, and an electrically conductive layer (eleventh conductive layer from the outermost layer) 331 in the structure shown in FIG. 7 in response to the application of the laser lights having the wavelengths $\lambda 1$=364 nm, $\lambda 2$=458 nm, $\lambda 3$=488 nm, $\lambda 4$=568 nm, and $\lambda 5$=647 nm. The detection unit 15 then outputs Raman signals RS1 to RS5, and sends these signals to the spectral processing unit 16 (see FIG. 1). The spectral processing unit 16 spectrally processes the Raman signals RS1 to RS5 sent from the detection unit 15.

Here, it should be noted that the Raman signal obtained by using the laser light having a long wavelength, more specifically, the laser light which penetrates the outermost layer into the depth of the layer under the outermost layer corresponds to its penetration depth, that is, a shift amount (cumulative information) from the outermost layer to an analysis target layer. This is because it is not possible to evaluate, from the cumulative information, what difference is there between the crystal structures of the respective layers, and thus some separating processing needs to be performed.

In the componential analysis apparatus according to the present embodiment, the spectral processing unit 16 performs differential processing of Raman spectrums and thereby calculates the differential spectrum in order to analyze depth direction information from the Raman signal sent from the detection unit 15 in addition to the vector processing of the Raman signal. The concept of the differential processing is more specifically described with reference to FIG. 8. FIG. 8 is a diagram again showing the structure of the three-dimensionally stacked semiconductor memory shown in FIG. 7, and further illustrating the penetration depths of the laser lights having the five wavelengths $\lambda 1$ to $\lambda 5$ and the concept of the differential processing.

Figure 8:
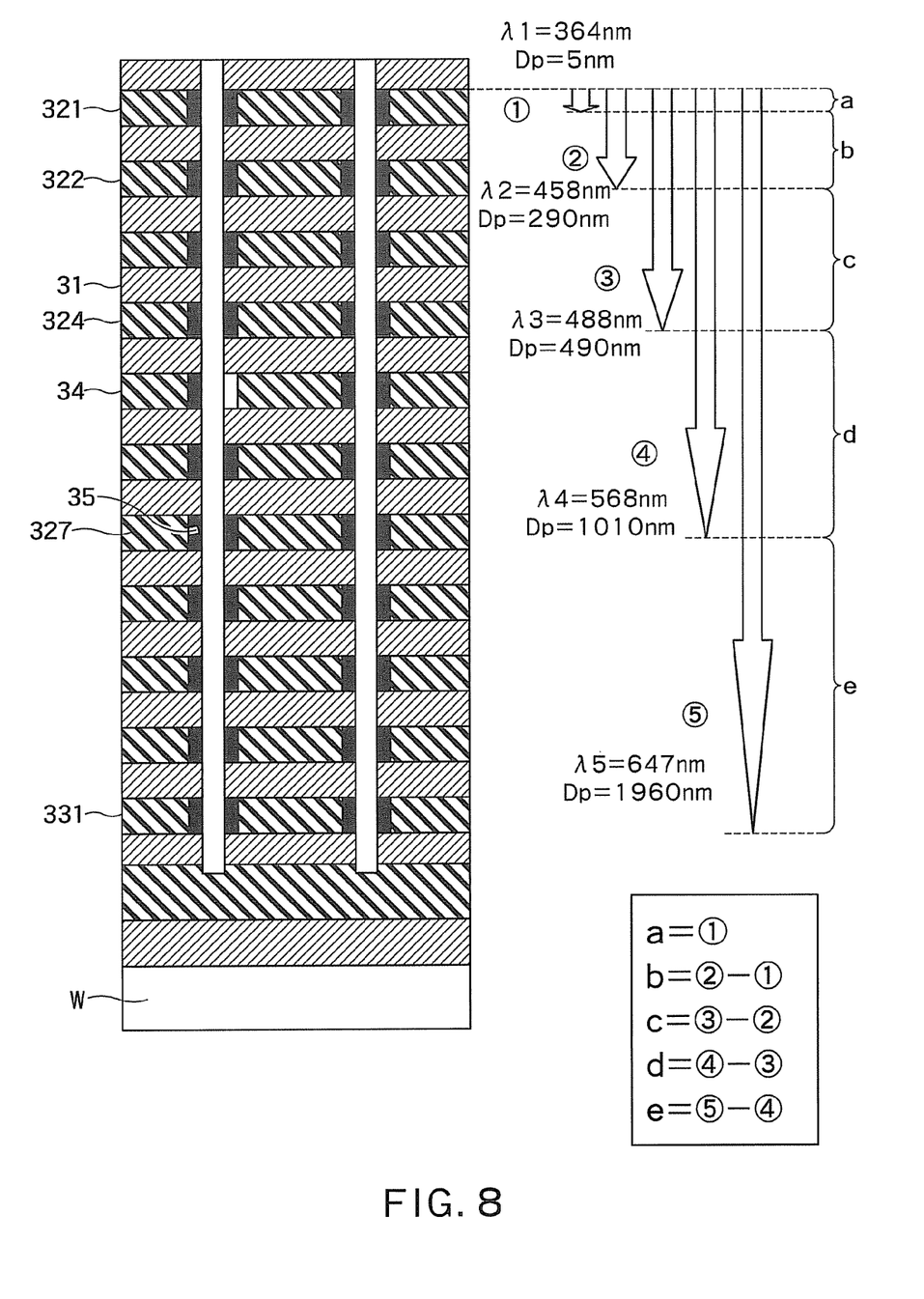
FIG. 8 is a diagram illustrating the penetration depths of laser lights and the concept of differential processing.

FIG. 8 shows the penetration depths (corresponding to the tips of arrows that respectively correspond to the Raman signals RS1 to RS5) of the laser light from the short-wavelength ($\lambda 1$) side to the laser light on the long-wavelength ($\lambda 5$) side. In the differential processing, the spectral processing unit 16 (see FIG. 1) redivides the three-dimensional structure by a definition different from that of the division in FIG. 7. As shown in FIG. 8, these divided regions are defined by five layers: an a-layer, a b-layer, a c-layer, a d-layer, and an e-layer. Information regarding the a-layer is estimated from the Raman signal RS1. Information regarding the b-layer is estimated from the difference between the Raman spectrum obtained by the processing of the Raman signal RS2 and the Raman spectrum obtained by the processing of the Raman signal RS1. Similarly, information regarding the c-layer is estimated from the difference between the Raman spectrum obtained by the processing of the Raman signal RS3 and the Raman spectrum obtained by the processing of the Raman signal RS2. Information regarding the d-layer is estimated from the difference between the Raman spectrum obtained by the processing of the Raman signal RS4 and the Raman spectrum obtained by the processing of the Raman signal RS3. Information regarding the e-layer is estimated from the difference between the Raman spectrum obtained by the processing of the Raman signal RS5 and the Raman spectrum obtained by the processing of the Raman signal RS4.

In the present embodiment, when the information regarding the b-layer is estimated, the b-layer corresponds to, for example, a first layer, the a-layer corresponds to, for example, a second layer, the Raman spectrum obtained by the processing of the Raman signal RS2 corresponds to, for example, a first Raman signal, and the Raman spectrum obtained by the processing of the Raman signal RS1 corresponds to, for example, a second Raman signal. Furthermore, in the present embodiment, when the information regarding the c-layer is estimated, the c-layer corresponds to, for example, the first layer, the b-layer corresponds to, for example, the second layer, the Raman spectrum obtained by the processing of the Raman signal RS3 corresponds to, for example, the first Raman signal, and the Raman spectrum obtained by the processing of the Raman signal RS2 corresponds to, for example, the second Raman signal. Similarly, in the present embodiment, when the information regarding the d-layer is estimated, the d-layer corresponds to, for example, the first layer, the c-layer corresponds to, for example, the second layer, the Raman spectrum obtained by the processing of the Raman signal RS4 corresponds to, for example, the first Raman signal, and the Raman spectrum obtained by the processing of the Raman signal RS3 corresponds to, for example, the second Raman signal. Moreover, in the present embodiment, when the information regarding the e-layer is estimated, the e-layer corresponds to, for example, the first layer, the d-layer corresponds to, for example, the second layer, the Raman spectrum obtained by the processing of the Raman signal RS5 corresponds to, for example, the first Raman signal, and the Raman spectrum obtained by the processing of the Raman signal RS4 corresponds to, for example, the second Raman signal.

Here, the integrated intensity of the Raman signal depends on the scattering volume of Raman scattering. Therefore, in the differential processing of the Raman spectrum, it is necessary to correct the Raman signal for a contribution of the scattering volume in advance.

Figure 9:
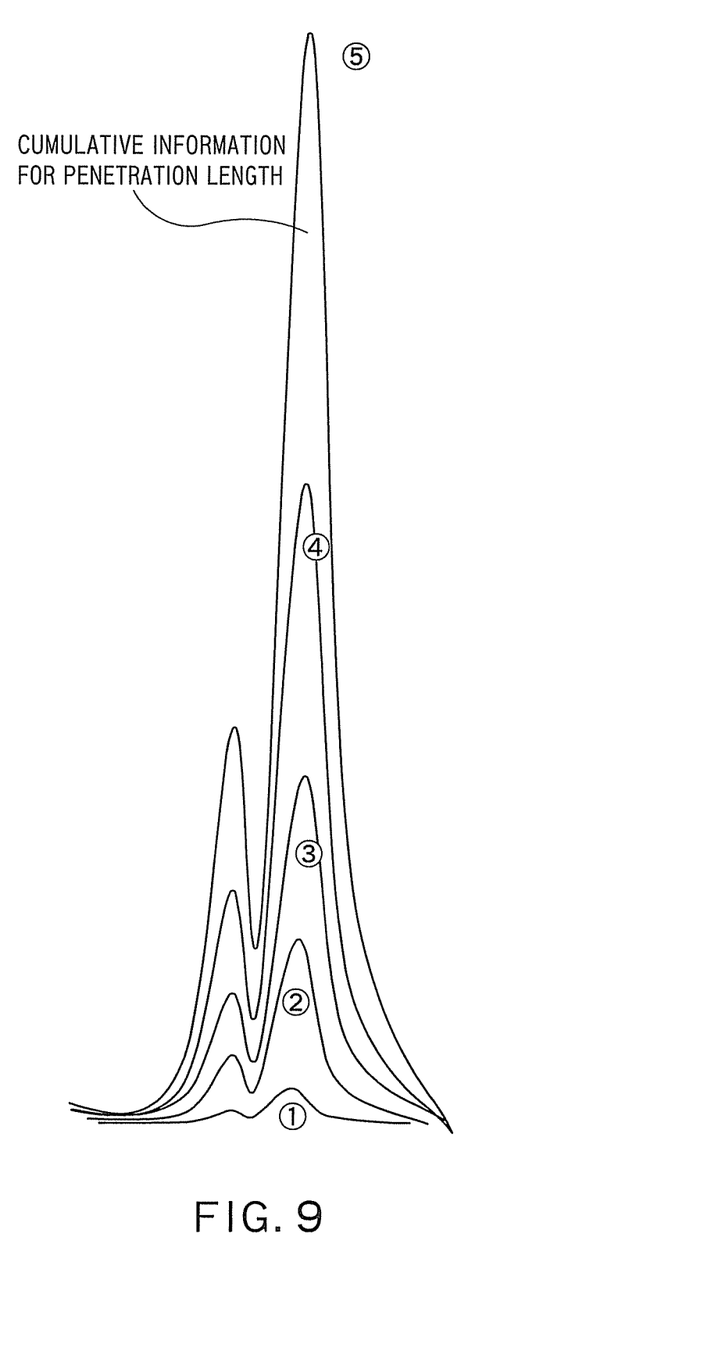
FIG. 9 is a diagram showing an example of changes of the Raman signals obtained in measurement of a sample equal to or more than the penetration depths of the laser lights in thickness by the use of five laser lights different to each other in wavelength.

FIG. 9 shows changes of the Raman signals RS1 to RS5 measured by the use of the laser lights having the wavelengths $\lambda 1$ to $\lambda 5$ in a sample which has a thickness equal to or more than the penetration depths. Since the penetration depth of the laser light determines the scattering volume, the use of a laser light having a longer wavelength increases the integrated intensity of the spectrum. Therefore, in order to perform the differential processing from the Raman signals measured at different wavelengths, it is necessary to correct for a contribution of the integrated intensity dependent on the scattering volume.

In the present embodiment, the detection unit 15 (see FIG. 1) uses, as a coefficient, the ratio (e.g. the ratio between the Raman signals RS1 and RS2 in the b-layer) of the scattering volumes of the laser lights of two wavelengths to be subjected to the differential processing, in order to perform a correction which multiplies the reciprocal number of the coefficient. Thus, the Raman signals of the layers divided by this correction are normalized to integrated intensity per unit volume, respectively, so that a signal comparison in a depth direction is made possible.

Figure 10:
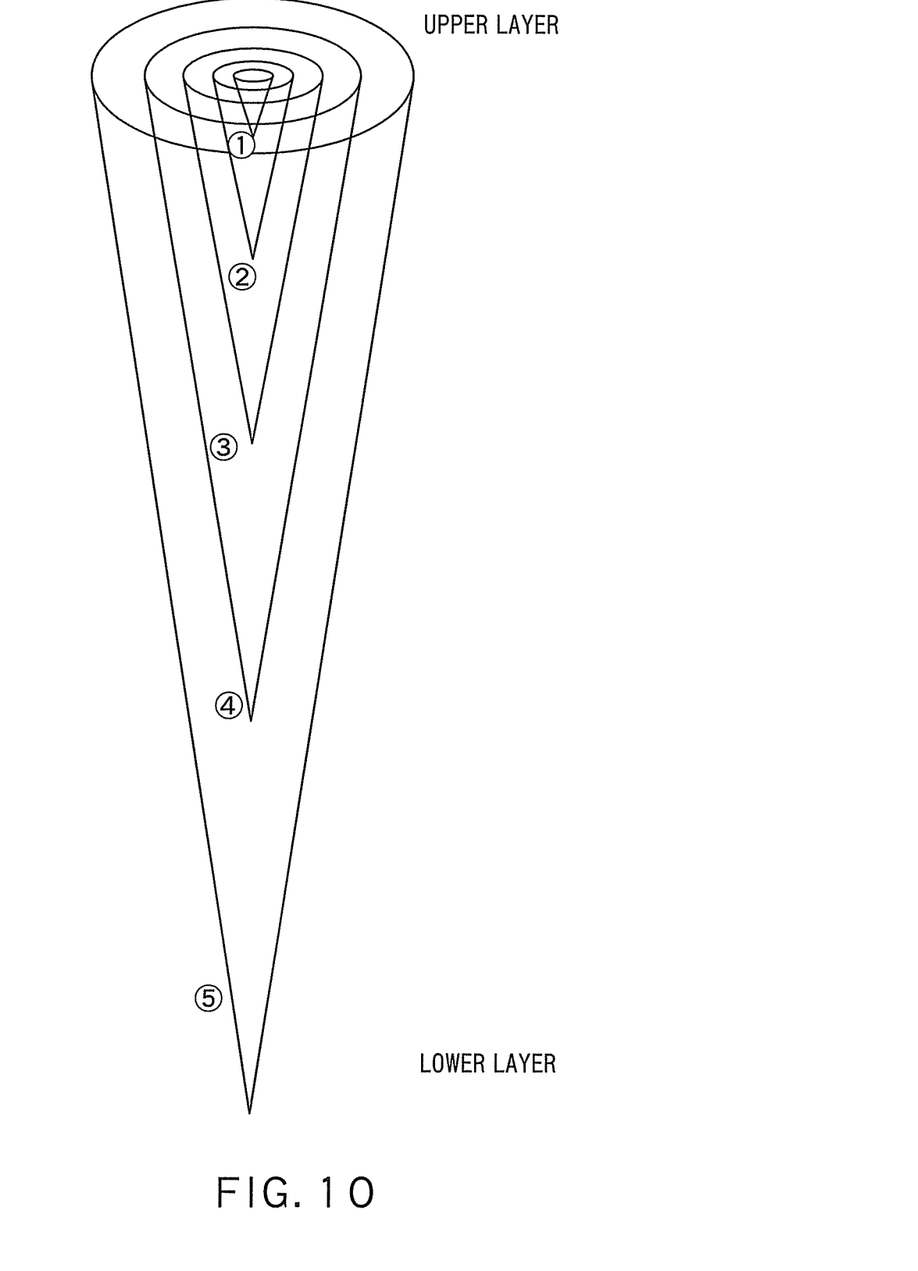
FIG. 10 is a schematic diagram showing a model of scattering volumes when the five laser lights shown in FIG. 9 are used.

FIG. 10 shows a model of scattering volumes when the laser lights of the wavelengths $\lambda 1$ to $\lambda 5$ are used. In FIG. 10, the scattering volume is conically modeled for simplification of explanation. An actual scattering volume is considered to be represented by a shape such as an extinction curve of light which exponentially decreases relative to the penetration depth of the laser light. Thus, for more accurate estimation, a calculation technique using the volume integral of an exponential function is also available.

The differential spectrum which has been processed and corrected as described above is sent to the analysis unit 21 from the spectral processing unit 16. The analysis unit 21 analyzes the sent differential spectrum to analyze the components of the material at the analysis target position. More specifically, the components of the material at the analysis target position are analyzed by the comparison between the reference spectrum (see FIG. 6) previously obtained for a plurality of kinds of component distributions and the differential spectrum.

The analysis unit 21 displays the analytic result on the display unit 19, and stores the analytic result in the memory MR2.

Figure 11:
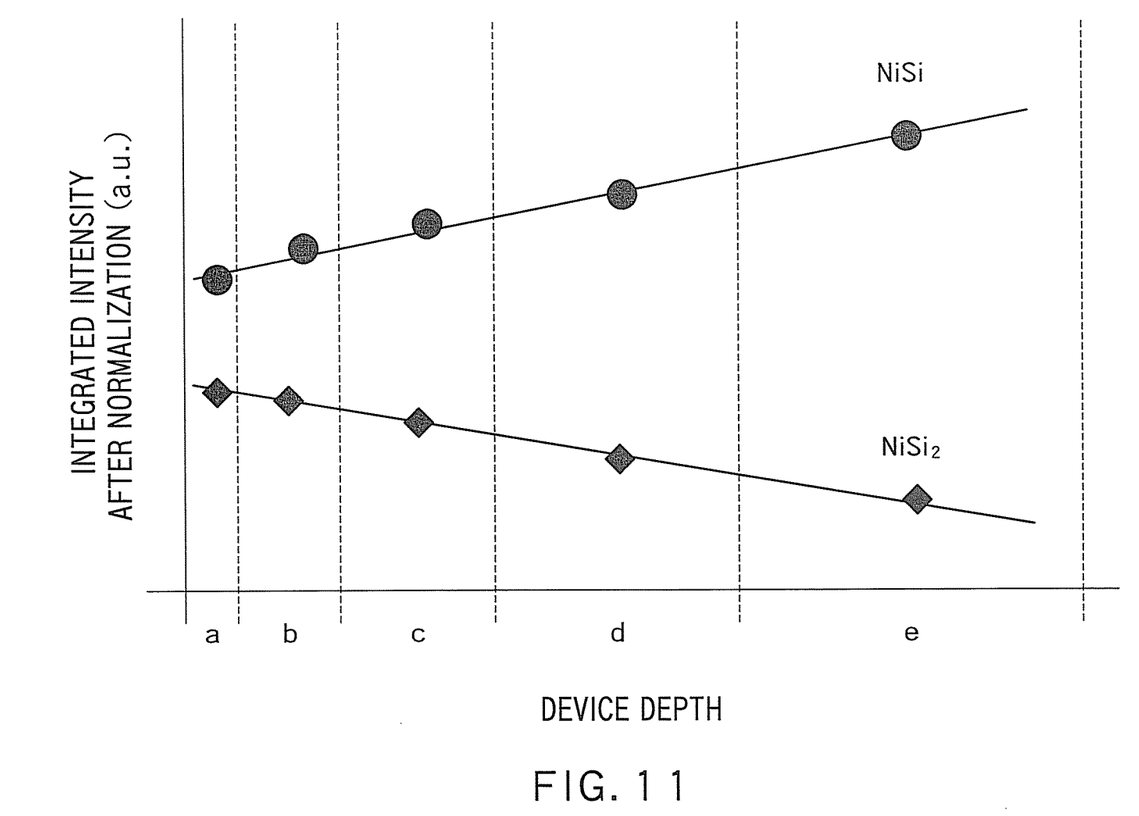
FIG. 11 is a graph showing an example of monitoring results of the Raman signals of nickel silicide in the three-dimensionally stacked semiconductor memory which are estimated by the componential analysis apparatus in FIG. 1.

FIG. 11 shows an example of the analytic result of the Raman signals by the componential analysis apparatus according to the present embodiment. The analysis target is the nickel silicide 35 of the three-dimensionally stacked semiconductor memory shown in FIG. 2. The integrated intensities of the Raman signals of NiSi and $NiSi_2$ are compared in the a-layer to the e-layer redivided in FIG. 8. It can then be estimated from FIG. 11 that the higher layers have a lower integrated intensity of NiSi and a higher integrated intensity of $NiSi_2$ and further progress in disilicidation.

In the above description, the structure including the three-dimensionally stacked semiconductor memory provided on the semiconductor substrate W is shown as the sample S. However, it should be understood that the sample which can be analyzed by the componential analysis apparatus according to the present embodiment is not limited to such a structure. For example, the sample may be a single thick layer designed to have the same components or a stack made of various different components.

For example, in an electric power generation cell provided in a photovoltaic generator, a single thick amorphous silicon layer is formed. However, the composition may vary in the surface layer and the bottom due to, for example, variations in a manufacturing process. For example, single crystal, polycrystal, and amorphous silicon may be mixed in a single layer. In this case, the componential analysis apparatus according to the present embodiment can be used to monitor whether the same structure is formed in the surface layer and in the bottom.

The componential analysis apparatus according to at least one embodiment described above includes the detection unit 15 and the analysis unit 21. The detection unit 15 spectrally processes first and second Raman signals obtained by the detection of Raman scattered lights respectively obtained from an analysis target first layer and from a second layer located closer to a surface layer than the first layer. The detection unit 15 thereby acquires first and second Raman spectrums, and acquires a differential spectrum in which the second Raman spectrum is subtracted from the first Raman spectrum. The analysis unit 21 analyzes the differential spectrum to analyze the components of the first layer. Consequently, nondestructive monitoring in the depth direction of the stack is also possible.

(B) Componential Analysis Method

Figure 12:
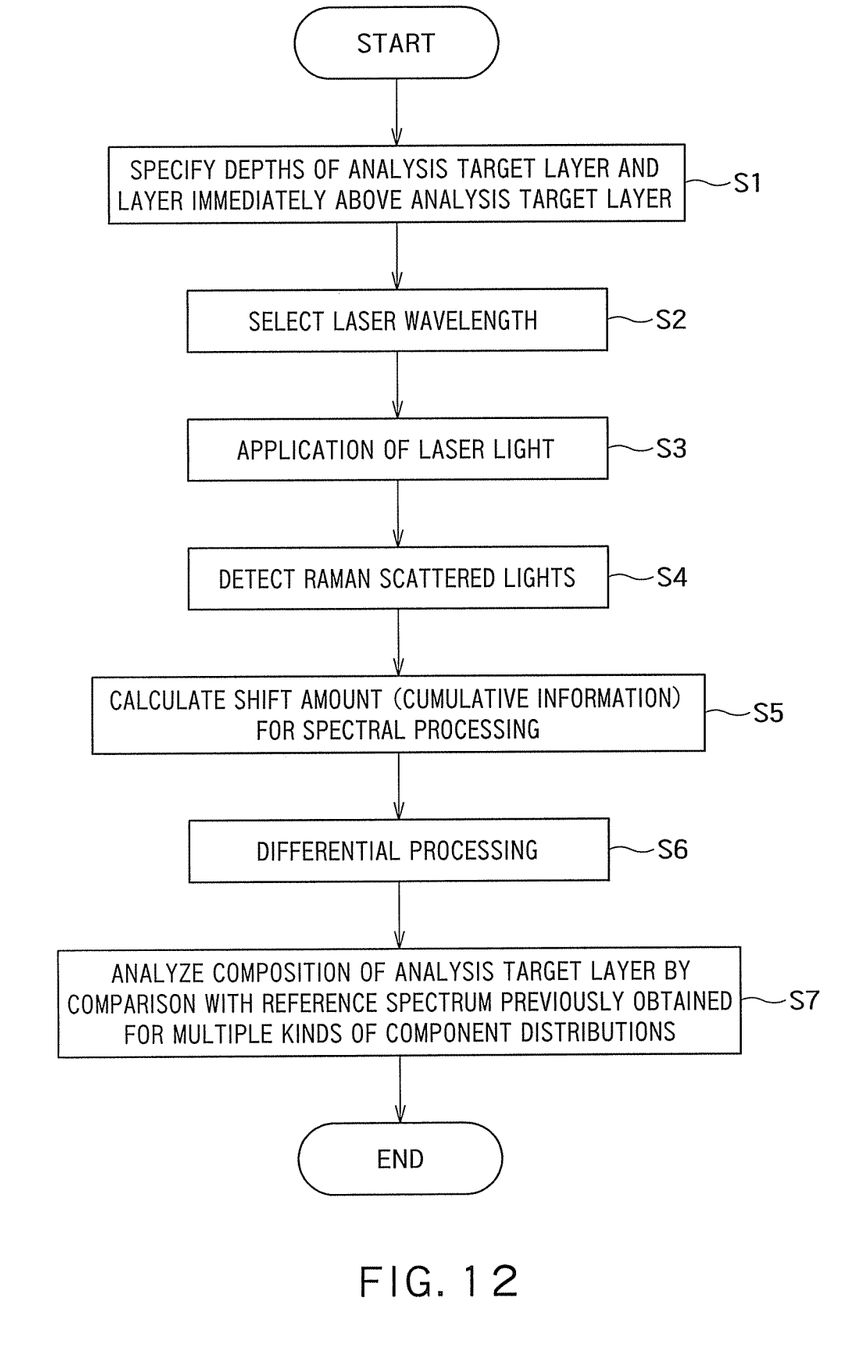
FIG. 12 is a flowchart showing a general process of a componential analysis method according to one embodiment.

A componential analysis method according to one embodiment is described with reference to FIG. 12. FIG. 12 is a flowchart showing a general procedure of the componential analysis method according to the present embodiment.

First, the depth of an analysis target layer in a sample structure is specified (step S1). Not only the depth of the target layer but also the depth of a layer immediately above the target layer is specified. Each numerical value of the depth may be previously found from design information, or may be sequentially found as preprocessing by the use of the spectroscopic ellipsometer (see the analysis position depth measurement unit 13 in FIG. 1).

A laser wavelength is then selected in accordance with the depths of the analysis target layer and the layer immediately above the analysis target layer (step S2), and the laser lights of the respective wavelengths are emitted and sequentially applied to the sample.

Raman scattered lights are generated from the sample in response to the application of the laser lights. These scattered lights are detected (step S4). Their Raman signals are acquired, and a shift amount is calculated for each of the Raman signals for spectral processing (step S5).

The obtained spectrums are then differentially processed (step S6). More specifically, the spectrum obtained from the Raman signal of the layer immediately above the analysis target layer is subtracted from the spectrum obtained from the Raman signal of the analysis target layer to acquire a differential spectrum. In this case, as described above, the ratio of the scattering volumes of the two laser wavelengths is used as a coefficient to perform correction processing which multiplies the reciprocal number of the coefficient.

Finally, the differential spectrum obtained in step S6 is compared with the reference spectrum previously obtained for a plurality of kinds of component distributions to analyze the composition of the analysis target layer (step S7). More specifically, the component distribution which provides the reference spectrum proximate to the differential spectrum is output as the composition of the analysis target layer.

According to the componential analysis method of at least one embodiment described above, first and second Raman signals are spectrally processed. The first and second Raman signals are obtained by the detection of Raman scattered lights respectively obtained from an analysis target first layer and from a second layer located closer to a surface layer than the first layer. First and second Raman spectrums are thereby acquired, and a differential spectrum in which the second Raman spectrum is subtracted from the first Raman spectrum is acquired and analyzed. Consequently, nondestructive monitoring in the depth direction of the stack is also possible.

(C) Manufacturing Method

When it is determined that the components of the stack vary in the depth direction by implementing the componential analysis method according to the present embodiment described above, the analytic result is fed back to an upstream manufacturing process. For example, measures are taken to change thermal conditions in the generation of metal silicide. It is thus possible to generate low-resistance metal silicide from the uppermost layer to the lowermost layer. When a variation of the components has resulted from the shortage of a thermal treatment, the metal silicide can be recovered by a repeated thermal treatment.

According to the manufacturing method of at least one embodiment described above, nondestructive monitoring in the depth direction of the stack is also possible. Therefore, it is possible to improve the yield of the manufacturing process and improve product quality by appropriate feedback to other manufacturing processes.

(D) Program and Recording Medium

A series of procedures in the componential analysis described above may be incorporated in a program, and read into and executed by a computer. This enables a series of procedures in the componential analysis described above to be carried out by use of a general-purpose computer connected to a general Raman spectroscope. A series of procedures of the componential analysis described above may be stored in a non-transitory recording medium such as a flexible disk or a CD-ROM as a program to be executed by the computer, and read into and executed by the computer. The recording medium is not limited to a portable medium such as a magnetic disk or an optical disk, and may be a fixed recording medium such as a hard disk drive or a memory. The program incorporating the series of procedures of the componential analysis described above may be distributed via a communication line (including wireless communication) such as the Internet. Moreover, the program incorporating the series of procedures of the sample structure analysis described above may be distributed in an encrypted, modulated or compressed state via a wired line or a wireless line such as the Internet or in a manner stored in a non-transitory recording medium.

(E) Others

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A componential analysis method comprising:
dividing a sample structure into at least a first layer to be analyzed and a second layer located closer to a surface layer of the sample than the first layer;
applying, to the sample, laser lights of a first and a second wavelength respectively corresponding to depths of the first and second layers;
detecting Raman scattered lights respectively obtained from the sample by the application of the laser lights and then outputting first and second Raman signals;
spectrally processing the first and second Raman signals to acquire first and second Raman spectrums;
correcting the first and second Raman signals by a contribution of a signal intensity change depending on a penetration depth of each of the first and second wavelengths;
acquiring a differential spectrum by subtracting the second Raman spectrum from the first Raman spectrum;
analyzing the differential spectrum; and
wherein the correcting the first and second Raman signals comprises calculating a ratio of scattering volumes of the laser lights of the first and second wavelengths, using the obtained ratio as a coefficient to multiply a reciprocal number of the coefficient by the first and second Raman signals, and thereby normalizing the first and second Raman signals to integrated intensity per unit volume.

2. The method of claim 1, wherein the analyzing the differential spectrum comprises comparing the differential spectrum with a reference spectrum previously obtained for a plurality of kinds of component distributions.

3. The method of claim 1, wherein:
the first and second layers are designed to comprise the same components, and
the analyzing the differential spectrum comprises examining whether the first layer is made of the same components as the second layer.

4. The method of claim 1, wherein:
the sample structure comprises a stack in which multi-layered insulating layers and multi-layered electrically conductive layers are alternately stacked, and
the first layer is an electrically conductive layer in which metal silicide is formed in the stack.

5. A non-transitory computer-readable recording medium containing a program which causes a computer connected to a Raman spectroscope to perform:
dividing a sample structure into at least a first layer to be analyzed and a second layer located closer to a surface layer of the sample than the first layer;
applying, to the sample, laser lights of a first and a second wavelength respectively corresponding to depths of the first and second layers;
detecting Raman scattered lights respectively obtained from the sample by the application of the laser lights and then outputting first and second Raman signals;
spectrally processing the first and second Raman signals to acquire first and second Raman spectrums;
correcting the first and second Raman signals by a contribution of a signal intensity change depending on a penetration depth of each of the first and second wavelengths;
acquiring a differential spectrum by subtracting the second Raman spectrum from the first Raman spectrum; and
analyzing the differential spectrum;

wherein the correcting the first and second Raman signals comprises calculating a ratio of scattering volumes of the laser lights of the first and second wavelengths, using the obtained ratio as a coefficient to multiply a reciprocal number of the coefficient by the first and second Raman signals, and thereby normalizing the first and second Raman signals to integrated intensity per unit volume.

6. The medium of claim 5, wherein the analyzing the differential spectrum comprises comparing the differential spectrum with a reference spectrum previously obtained for a plurality of kinds of component distributions.

* * * * *